United States Patent
Phan et al.

(10) Patent No.: US 9,023,826 B2
(45) Date of Patent: May 5, 2015

(54) COMPOSITIONS CONTAINING ADENOSINE AND THE HYDROTROPES CAFFEINE AND NICOTINAMIDE FOR COSMETIC USE

(71) Applicant: L'Oreal S.A., Paris (FR)

(72) Inventors: Zhi Phan, Fort Lee, NJ (US); Jean-Thierry Simonnet, Mamaroneck, NY (US)

(73) Assignee: L'Oreal S.A., Paris (FR)

( * ) Notice: Subject to any disclaimer, the term of this patent is extended or adjusted under 35 U.S.C. 154(b) by 102 days.

(21) Appl. No.: 13/650,774

(22) Filed: Oct. 12, 2012

(65) Prior Publication Data

US 2014/0107059 A1 Apr. 17, 2014

(51) Int. Cl.
| | | |
|---|---|---|
| A61Q 19/08 | (2006.01) | |
| A61K 47/22 | (2006.01) | |
| A61K 31/7076 | (2006.01) | |
| A61K 31/4188 | (2006.01) | |
| A61K 31/465 | (2006.01) | |
| A61K 8/49 | (2006.01) | |
| A61K 8/368 | (2006.01) | |
| A61K 8/42 | (2006.01) | |
| A61K 8/60 | (2006.01) | |
| A61K 8/67 | (2006.01) | |

(52) U.S. Cl.
CPC ............... *A61Q 19/08* (2013.01); *A61K 47/22* (2013.01); *A61K 31/7076* (2013.01); *A61K 31/4188* (2013.01); *A61K 31/465* (2013.01); *A61K 8/4926* (2013.01); *A61K 8/4946* (2013.01); *A61K 8/368* (2013.01); *A61K 8/42* (2013.01); *A61K 8/492* (2013.01); *A61K 8/4953* (2013.01); *A61K 8/606* (2013.01); *A61K 8/675* (2013.01); *A61K 2800/49* (2013.01)

(58) Field of Classification Search
CPC ... C07H 19/16; A61K 31/7076; A61K 47/00; A61K 8/606; A61K 8/4973; A61Q 19/00; A61Q 90/00
See application file for complete search history.

(56) References Cited

U.S. PATENT DOCUMENTS

| | | |
|---|---|---|
| 3,501,409 A | 3/1970 | Matson |
| 3,839,210 A | 10/1974 | Beiswanger et al. |
| 4,680,143 A | 7/1987 | Edge et al. |
| 5,532,012 A | 7/1996 | Balentine et al. |
| 5,686,082 A | 11/1997 | N'Guyen |
| 6,121,209 A | 9/2000 | Watts et al. |
| 6,331,520 B1 | 12/2001 | Richardson |
| 6,355,657 B1 | 3/2002 | Osborne |
| 6,423,327 B1 | 7/2002 | Dobson, Jr. et al. |
| 6,479,442 B1 | 11/2002 | Berube et al. |
| 6,645,513 B2 | 11/2003 | Dobson, Jr. et al. |
| 6,646,035 B2 | 11/2003 | Koch et al. |
| 6,733,797 B1 | 5/2004 | Summers |
| 6,949,496 B1 | 9/2005 | Boutique et al. |
| 7,452,549 B2 | 11/2008 | Hasler-Nguyen et al. |
| 2002/0086042 A1 | 7/2002 | Delrieu et al. |
| 2002/0110604 A1 | 8/2002 | Babish et al. |
| 2003/0031715 A1 | 2/2003 | Park et al. |
| 2003/0206972 A1 | 11/2003 | Babish et al. |
| 2004/0146474 A1 | 7/2004 | Galey |
| 2005/0158271 A1 | 7/2005 | Lee et al. |
| 2005/0266121 A1 | 12/2005 | Lines et al. |
| 2006/0110439 A1 | 5/2006 | Tobia et al. |
| 2007/0208088 A1 | 9/2007 | Lipshutz |
| 2007/0232561 A1 | 10/2007 | Leung et al. |
| 2008/0095866 A1 | 4/2008 | Declercq et al. |
| 2008/0176956 A1 | 7/2008 | Hsu |
| 2008/0219927 A1 | 9/2008 | Thakur et al. |
| 2009/0110674 A1 | 4/2009 | Loizou |
| 2009/0233876 A1 | 9/2009 | Auriol et al. |
| 2010/0047297 A1 | 2/2010 | Petersen |
| 2011/0033525 A1 | 2/2011 | Liu |
| 2011/0067294 A1 | 3/2011 | Ng et al. |
| 2011/0136245 A1 | 6/2011 | Parker |
| 2011/0152214 A1 | 6/2011 | Boison et al. |
| 2011/0305737 A1* | 12/2011 | Alexiades-Armenakas .. 424/401 |
| 2012/0071550 A1 | 3/2012 | Zelkha et al. |
| 2013/0309188 A1* | 11/2013 | Ishihara et al. ................. 424/62 |

FOREIGN PATENT DOCUMENTS

| | | | | |
|---|---|---|---|---|
| KR | 1020100004547 | * | 1/2010 | ............... A61K 8/89 |
| WO | WO-2013016257 A1 | | 1/2013 | |

OTHER PUBLICATIONS

Kadir, R., Stempler, D., Liron, Z., & Cohen, S. (1989). Penetration of theophylline and adenosine into excised human skin from binary and ternary vehicles: effect of a nonionic surfactant. Journal of pharmaceutical sciences, 78(2), 149-153.*

Lee et al., KR 10-2010-0004547, Jan. 2010, machine translation. Retreived on Apr. 3, 2103 from http://translate.google.com.*

Suzuki, H. et al., "Mechanistic Studies on Hydrotropic Solubilization of Nifedipine in Nicotinamide Solution." *Chem. Pharm. Bull.* 46(1), 125-130 (1998).

Evstigneev, M.P. et al., "Effect of a mixture of caffeine and nicotinamide on the solubility of vitamin (B2) in aqueous solution," *European Journal of Pharmaceutical Sciences* 28, 59-66 (2006).

Da Silva, R.C. et al., "Investigations on the mechanism of aqueous solubility increase caused by some hydrotropes." *Thermochimica Acta* 328, 161-167 (1999).

(Continued)

*Primary Examiner* — Shaojia Anna Jiang
*Assistant Examiner* — Dale R Miller
(74) *Attorney, Agent, or Firm* — Novak Druce Connolly Bove + Quigg LLP

(57) ABSTRACT

The present invention provides aqueous compositions comprising (a) at least one compound selected from the group consisting of adenosine and adenosine analogs, and (b) at least one hydrotrope in an amount effective to solubilize said at least one compound (a) in water, for cosmetic uses.

7 Claims, No Drawings

(56) References Cited

OTHER PUBLICATIONS

Huh, K.M. et al., "A new hydrotropic block copolymer micelle system for aqueous solubililzation of paclitaxel." *Journal of Controlled Release* 126, 122-129 (2008).

Takahashi, K. et al., "Application of hydrotropy to transdermal formulations: hydrotropic solubilization of polyol fatty acid monoesters in water and enchancement effect on skin permeation of 5-FU." *Journal of Pharmacy and Pharmacology* 63, 1008-1014 (2011).

Nicoli, S. et al., "Association of nicotinamide with parabens: Effect on solubility, partition and transdermal permeation." *European Journal of Pharmaceutics and Biopharmaceutics* 69, 613-621 (2008).

Nidhi, K. et al., "Hydrotropy: A Promising Tool for Solubility Enhancement: A Review." *International Journal of Drug Development & Research* 3(2), 26-33 (2011).

\* cited by examiner

COMPOSITIONS CONTAINING ADENOSINE AND THE HYDROTROPES CAFFEINE AND NICOTINAMIDE FOR COSMETIC USE

BACKGROUND OF THE INVENTION

The present invention relates to aqueous compositions comprising adenosine or an adenosine analogue, and at least one hydrotrope, for cosmetic use.

Adenosine is an endogenous purine nucleoside that modulates many physiological processes. It is known that in regard to stress or injury, adenosine primarily provides cytoprotection preventing tissue damage in disorders like hypoxia, ischemia and seizure (Sebastião A M, Ribeiro J A (2009), "Adenosine receptors and the central nervous system", Handb Exp Pharmacol. 193:471-534) Adenosine is also believed to be an anti-inflammatory agent at one of its cellular signaling receptors, A2A. (Trevethick M A, Mantell S J, Stuart E F, Barnard A, Wright K N, Yeadon M (October 2008), "Treating lung inflammation with agonists of the adenosine A2A receptor: promises, problems and potential solutions". Br. J. Pharmacol. 155 (4): 463-74)) Topical treatment of adenosine on wound sites can drastically increase tissue repair and reconstruction. (Haskó G, Linden J, Cronstein B, Pacher P (September 2008). "Adenosine receptors: therapeutic aspects for inflammatory and immune diseases". Nat Rev Drug Discov 7 (9): 759-70; Nakav S, Chaimovitz C, Sufaro Y (2008). Bozza, Patricia. ed. "Anti-Inflammatory Preconditioning by Agonists of Adenosine A1 Receptor". PLoS ONE 3 (5): e2107)

In the cosmetic domain, adenosine and its analogues are important active compounds for skin anti-aging due to its function on increasing DNA/protein synthesis in dermal cells. It has been broadly applied in many skin care products to improve the visual appearance of skin, such as soften fine lines and reduce wrinkles of skin and relax the muscles involved in facial movement and expression.

However, the solubility of adenosine is very limited, especially in water, which suppresses its biological potential in cosmetics. Thus, there remains a need for methods for improving the water solubility of adenosine for cosmetic use.

Published U.S. application 20040146474, L'Oreal, discloses methods for softening lines and relaxing the skin with adenosine and adenosine analogues. U.S. Pat. Nos. 6,423,327 and 6,645,513, University of Massachusetts, disclose treatment of skin with adenosine or an adenosine analogue. Published U.S. application 20070232561, King Pharmaceuticals Inc., discloses pharmaceutical compositions for promoting wound healing. The pharmaceutical compositions contain high concentration (10 to 70% w/w) of glycols and a thickening agent, and achieved a final concentration of 0.00001 to 0.10% w/w for adenosine analogues.

Published U.S. application 20080219927, A. B. Thakur et al., discloses adenosine derivative formulations for medical imaging. The formulations contain a solvent made up of water and hydroxypropyl-β-cyclodextrin to form a stable composition of adenosine analogues or derivatives that can be used for myocardial perfusion imaging. Published U.S. application 20110152214, Trustees of Tufts College, discloses a silk polymer-based adenosine release system with therapeutic potential for treatment of epilepsy.

BRIEF SUMMARY OF THE INVENTION

The invention provides aqueous compositions comprising (a) at least one compound selected from the group consisting of adenosine and adenosine analogues, and (b) at least one hydrotrope in an amount effective to solubilize the at least one compound of (a) in water. The compound of component (a) can be adenosine, or an adenosine analogue, or any combination of adenosine analogues or adenosine and adenosine analogue(s). The hydrotrope can be a cosmetically acceptable hydrotrope, such as nicotinamide, caffeine, sodium PCA, sodium salicylate, urea, or hydroxyethyl urea.

Another aspect of the invention provides a method for preparing an aqueous composition comprising including in the composition (a) at least one compound selected from the group consisting of adenosine and adenosine analogues, and (b) at least one hydrotrope in an amount effective to solubilize the at least one compound of (a) in water.

A further aspect of the invention provides a method comprising applying an aqueous composition to skin, the aqueous composition comprising (a) at least one compound selected from the group consisting of adenosine and adenosine analogues, and (b) at least one hydrotrope in an amount effective to solubilize said at least one compound (a) in the water phase.

These and other aspects of the invention are set out in the appended claims, and described in greater detail in the detailed description of the invention.

DETAILED DESCRIPTION OF THE INVENTION

The present invention provides aqueous compositions comprising (a) at least one compound selected from the group consisting of adenosine and adenosine analogues, and (b) at least one hydrotrope in an amount effective to solubilize said at least one compound (a) in water, for cosmetic uses. The hydrotrope, such as a cosmetically acceptable hydrotrope, improves the water solubility of adenosine or adenosine analogue. The hydrotropes can be used to formulate adenosine or adenosine analogue in all cosmetic formulas that contain water, for topical application, injection or oral administration.

Cosmetic uses of the compositions include antiaging products, skin care products, and products to improve the visual appearance of skin, such as soften fine lines, reduce skin wrinkles, and relax the muscles of the face.

Adenosine and adenosine analogues are poorly water soluble. Applicants have discovered that hydrotropes can dramatically increase the solubility of these poorly water soluble compounds in water by orders of magnitude. The aqueous compositions contain adenosine or adenosine analogue in greater percentage amounts than aqueous compositions in which the hydrotrope is not present. Applicants have also found that a combination of hydrotropes, such as the combination of caffeine and nicotinamide, is more efficient than either one alone for increasing the water solubility of adenosine.

Hydrotropes (or hydrotropic agents) are a diverse class of water-soluble compounds that characterized by an amphiphilic molecular structure and ability to dramatically increase the solubility of poorly soluble organic molecules in water.

Most hydrotropes have aromatic structure with an ionic moiety, while some of them are linear alkyl chains, as listed in the table below. Although hydrotropes noticeably resemble surfactants and have the ability to reduce surface tension, their small hydrophobic units and relatively shorter alkyl chain distinguish them as a separate class of amphiphiles. Consequently their hydrophobicity is not sufficient enough to create well organized self-associated structures, such as micelles, even with a high concentration.

Common hydrotropic molecules include: sodium 1,3-benzenedisulfonate, sodium benzoate, sodium 4-pyridinecarboxylate, sodium salicylate, sodium benzene sulfonate, caffeine, sodium p-toluene sulfonate, sodium butyl monoglycolsulfate, 4-aminobenzoic acid HCl, sodium cumene sulfonate, N,N-diethylnicotinamide, N-picolylnicotinamide, N-allylnicotinamide, 2-methacryloyloxyethyl phosphorylcholine, resorcinol, butylurea, pyrogallol, N-picolylacetamide 3.5, procaine HCl, proline HCl, nicotinamide, pyridine, 3-picolylamine, sodium ibuprofen, sodium xylenesulfonate, ethyl carbamate, pyridoxal hydrochloride, sodium benzoate, 2-pyrrolidone, ethylurea, N,N-dimethylacetamide, N-methylacetamide, and isoniazid. Hydrotropes can be found in Lee J. et al., "Hydrotropic Solubilization of Paclitaxel: Analysis of Chemical Structures for Hydrotropic Property", Pharmaceutical Research, Vol. 20, No. 7, 2003; and Lee S. et al., "Hydrotropic Polymers: Synthesis and Characterization of Polymers Containing Picolylnicotinamide Moieties", Macromolecules, 36, 2248-2255, 2003.

Cosmetically acceptable hydrotropes refers to hydrotropes that can be used in cosmetic compositions. While hydrotropes represent a broad class of molecules used in various fields, cosmetic applications will be limited due to safety and tolerance restrictions. Suitable hydrotropes for use in cosmetics include, but are not limited to, the hydrotropes listed below:

| Name of hydrotropes | Structure |
|---|---|
| Nicotinamide (Vit B3) | 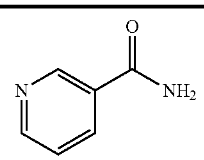 |
| Caffeine | 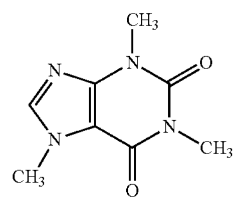 |
| Sodium PCA | 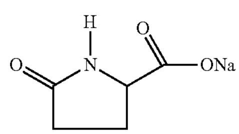 |
| Sodium Salicylate | 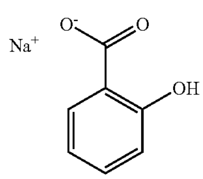 |
| Urea | 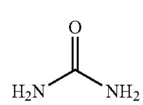 |
| Hydroxyethyl urea | 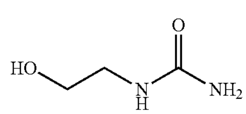 |

The suitability of a hydrotrope for use in cosmetic compositions can be determined using tests known in the art for determining effects on skin, and toxicity to humans.

At least one hydrotrope refers to one or a combination of two or more hydrotropes. One or combination of two or more hydrotropes can be used to improve the solubility of adenosine or adenosine analogue in water.

The at least one hydrotrope is present in the aqueous composition in amounts effective to increase the solubility of adenosine or adenosine analogue in water. The amount of hydrotrope will vary depending on the hydrotrope and the type and amount of adenosine or adenosine analogue. The amount of hydrotrope present in the aqueous compositions can range from about 0.1 to about 20%; about 0.1 to about 10%; or about 1% to about 50%, based on the total weight of the composition.

Increasing the water solubility of adenosine or adenosine analogue refers to increasing the solubility of adenosine or adenosine analogue in water in comparison with solubility of the adenosine or adenosine analogue in water in the absence of the hydrotrope or hydrotropes.

An advantage of using hydrotropes is that, once a stable solution is obtained, further dilution won't influence the stability. This is very different from organic solvents like glycols that are commonly used to increase the water solubility of adenosine. Typically, an aqueous dilution of organic solvents with pre-dissolved adenosine results in crystallization or precipitation.

The at least one compound selected from the group consisting of adenosine and adenosine analogues can be adenosine, or an adenosine analogue, or any combination of adenosine analogues or adenosine and adenosine analogue(s). Suitable adenosine analogues include agonists of adenosine receptors and compounds increasing intra- or extra-cellular adenosine levels.

Examples of adenosine analogues include: 2'-deoxyadenosine; 2',3'-isopropoylidene adenosine; toyocamycin; 1-methyladenosine, N-6-methyladenosine; adenosine N-oxide; 6-methylmercaptopurine riboside; 6-chloropurine riboside; 5'-adenosine monophosphate; 5'-adenosine diphosphate and 5'-adenosine triphosphate.

Other adenosine analogues include agonists of adenosine receptors, including phenylisopropyl adenosine (PIA), 1-methylisoguanosine, $N^6$-cyclohexyl adenosine (CHA), $N^6$-cyclopentyl adenosine (CPA), 2-chloro-N-6-cyclopentyladenosine, 2-chloroadenosine, $N^6$-phenyladenosine, 2-phenylaminoadenosine, MECA, $N^6$-phenethyladenosine, 2-p-(2-carboxyethyl)-phenethyl-amino-5'-N-eth-ylcarboxamido-adenosine (CGS-21680), N-ethylcarboxamido-adenosine (NECA), 5'-(N-cyclopropyl)-carboxamidoadenosine, DPMA (PD 129,944) and metrifudil.

Other adenosine analogues include compounds which increase the intracellular concentration of adenosine such as erythro-9-(2-hydroxy-3-n-onyl) adenine (EHNA) and iodotubercidin.

Other adenosine analogues also include salts and esters of adenosine.

Adenosine or adenosine analogue is solubilized in the aqueous compositions, and the amount of adenosine or adenosine analogue will depend on the type and amount of the hydrotrope(s) present in the aqueous compositions, as well as the specific adenosine analogue. The amount of adenosine or adenosine analogue present in the aqueous compositions can range from about 0.01% to about 20%; about 0.1% to about 10%; or about 0.1 to about 5% based on the total weight of the composition.

The aqueous compositions can also comprise at least one additive conventionally used in the cosmetics field which does not affect the properties of the compositions according to the invention, such as thickeners, fragrances, pearlescent agents, preservatives, sunscreens, anionic or nonionic or cationic or amphoteric polymers, proteins, protein hydrolysates, fatty acids, such as 18-methyleicosanoic acid, vitamins, panthenol, silicones, vegetable, animal, mineral or synthetic oils, gelling agents, antioxidants, solvents, fragrances, fillers, screening agents, odor absorbers and coloring materials. These additives can be present in the composition according to the invention in proportions which are not limited, but which advantageously fall in the range from 0 to 50% by weight, with respect to the total weight of the composition.

The composition comprises from about 1 to 99.9% by weight of water, with respect to the total weight of the composition. The amount of water in the composition can range from about 1 to 99.5%; about 1 to 60%; or about 1 to 50%, based on the total weight of the composition.

The pH of the aqueous compositions is not limited but is generally between 2 and 12, or between 3 and 9. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Generally, any composition of the invention can be ingested, injected or topically applied to the skin (over any cutaneous region of the body) or to the mucous membranes (oral, jugal, gingival, genital, conjunctival, and the like). Depending on the method of administration under consideration, the composition can be provided in any dosage form normally used.

For topical application to the skin, the composition can have the form in particular of aqueous or oily solutions or of dispersions of the lotion or serum type, of emulsions with a liquid or semi-liquid consistency of the milk type, obtained by dispersion of a fatty phase in an aqueous phase (O/W) or vice versa (W/O), or of suspensions or emulsions with a soft consistency of the aqueous or anhydrous gel or cream type, or else of microcapsules or microparticles, or of vesicular dispersions of ionic and/or nonionic type or of foams. These compositions are prepared according to the usual methods.

For injection, the composition can be provided in the form of aqueous or oily lotions or in the form of serums. For the eyes, the composition can be provided in the form of drops and, for ingestion, it can be provided in the form of capsules, granules, syrups or tablets.

The amounts of the various constituents of the compositions according to the invention are those conventionally used in the fields under consideration.

In the cosmetics field, these compositions constitute in particular creams for cleaning, protecting, treating or caring for the face, for the hands, for the feet, for the major anatomical folds or for the body (for example, day creams, night creams, make-up-removing creams, foundation creams or sun creams), liquid foundations, make-up-removing milks, protective or care body milks, sun milks, lotions, gels or foams for caring for the skin, such as cleansing lotions, sun lotions, artificial tanning lotions, bath compositions, deodorizing compositions comprising a bactericidal agent, after-shave gels or lotions, depilatory creams, compositions for countering insect stings or bites, pain-relieving compositions or compositions for treating certain skin diseases, such as eczema, rosacea, psoriasis, lichen and severe pruritus.

Another aspect of the invention provides a method for preparing the aqueous compositions comprising including in the composition at least one compound selected form the group consisting of adenosine and adenosine analogues and at least one hydrotrope in an amount sufficient to solubilize the adenosine and/or adenosine analogue(s) in water. A hydrotrope solution is prepared by completely dissolving one or more hydrotropic agents into water. Adenosine or adenosine analogue is then added in and mixed using stirring bar or any other mixer. Solubilization of adenosine and/or adenosine analogue(s) occurs within minutes, and mixing is continued until the maximum concentration achieved, which was defined as the solubility of the compound(s) under that condition. A clear stable solution with a concentration that does not exceed the solubility would be ready after more than one hour of mixing. No heat is necessary by following this procedure to dissolve adenosine or adenosine analogue. Everything is prepared at room temperature. This is extremely useful to protect the activity of certain compounds and also makes the process much easier.

EXAMPLES

Example 1

After the hydrotrope solution was prepared at certain concentrations by completely dissolving one or more hydrotropic agents into water, adenosine was added in and mixed using stirring bar or any other mixer, solubilization happened immediately and kept going on till the maximum concentration achieved, which was defined as the solubility of adenosine under that condition. A clear stable solution with a concentration that does not exceed the solubility would be ready after >1 hour mixing. No heat is necessary by following this procedure to dissolve adenosine. Everything is prepared at room temperature.

The water solubility of caffeine is ~2%, which limits its function as a hydrotropic agent. By mixing with nicotinamide, the solubility of caffeine can be increased to 5% or even higher. And the combination of caffeine and nicotinamide is more efficient than any one of themselves. Here the combination of 5% nicotinamide and 5% caffeine in water was used to solubilize adenosine, and a stable clear solution with 3% (w/w) adenosine was obtained.

| Name | Type | Solubility in water without hydrotropes % (w/w) | Solubility in water with hydrotropes % (w/w) |
|---|---|---|---|
| Adenosine | nucleoside | <0.5 | >3 |

As shown in above table, the solubility of adenosine in water was dramatically increased. Additionally, this solution of adenosine/hydrotropes in water is stable to be further diluted or concentrated in cosmetic formulas once we keep the ratio between hydrotropes and adenosine. Therefore, this solubility can be the final weight concentration in cosmetic formulae.

Example 2

Preparation A

| Phase | Component | Weight % of total |
|---|---|---|
| A | BIS-PEG/PPG-14/14 DIMETHICONE (and) DIMETHICONE | 4 |
| A | Dimethicone (and) dimethiconol | 1 |
| A | Dimethicone | 10 |
| B1 | Water | 43.95 |

-continued

| Phase | Component | Weight % of total |
|---|---|---|
| B1 | Nicotinamide | 5 |
| B1 | Caffeine | 5 |
| B1 | Adenosine | 3 |
| B2 | Glycerin | 15 |
| B2 | Propylene glycol | 5 |
| B3 | Water | 5 |
| B3 | Preservatives | 0.25 |
| B3 | Sodium citrate | 0.2 |
| B3 | Sodium chloride | 0.8 |
| C | Ethanol | 3 |
| C | Preservatives | 0.6 |
| D | Silica silylate | 0.7 |

Preparation A was prepared as follows. Phase A components were mixed together at room temperature. Phase B1 and Phase B2 were premixed in separate containers at room temperature until clear solutions were obtained. Phase B3 was mixed while heated to 75-80° C. until it was clear. Phase B2 and Phase B3 were added into Phase B1 while mixing. Then Phase B was slowly added into Phase A while mixing (as viscosity increased, the mixing speed was appropriately increased). When the addition was finished, mixing was continued for an additional 10 minutes before adding premixed Phase C. Phase D was slowly added while mixing till it was thoroughly dispersed, and the desired emulsion was obtained.

What is claimed is:

1. An aqueous, cosmetic composition comprising:
   (a) about 3% by weight, based on the total weight of the composition, of adenosine, and
   (b) hydrotropes in an amount effective to solubilize said adenosine in water, said hydrotropes comprising caffeine and nicotinamide, wherein:
   (i) the amount of said caffeine is about 5% by weight, based on the total weight of the composition, and
   (ii) the amount of said nicotinamide is about 5% by weight, based on the total weight of the composition.

2. A method for preparing an aqueous cosmetic composition comprising mixing:
   (a) about 3% by weight, based on the total weight of the composition, of adenosine, and
   (b) hydrotropes in an amount effective to solubilize said adenosine in water, said hydrotropes comprising caffeine and nicotinamide, wherein:
   (i) the amount of said caffeine is about 5% by weight, based on the total weight of the composition, and
   (ii) the amount of said nicotinamide is about 5% by weight, based on the total weight of the composition.

3. A method for improving the visual appearance of skin comprising applying a composition of claim 1 to the skin.

4. The cosmetic composition of claim 1, wherein the composition is in the form of an emulsion.

5. An aqueous, cosmetic, skin-care composition comprising:
   (a) about 3% by weight, based on the total weight of the composition, of adenosine, and
   (b) hydrotropes in an amount effective to solubilize said adenosine in water, said hydrotropes comprising both caffeine and nicotinamide, wherein:
   (i) the amount of said caffeine is 5% by weight, based on the total weight of the composition, and
   (ii) the amount of said nicotinamide is 5% by weight, based on the total weight of the composition,
   wherein said composition is in the form of an emulsion.

6. The composition of claim 5, comprising:
   (a) about 3% by weight of adenosine, based on the total weight of the compositions;
   (b) about 5% by weight of caffeine and about 5% by weight of nicotinamide 7. The composition of claim 5, further comprising dimethicone and ethanol.

* * * * *